United States Patent [19]

Barkalow

[11] 4,326,507

[45] Apr. 27, 1982

[54] CPR PROTOCOL AND CARDIOPULMONARY RESUSCITATOR FOR EFFECTING THE SAME

[75] Inventor: Clare E. Barkalow, Comstock Park, Mich.

[73] Assignee: Michigan Instruments, Inc., Grand Rapids, Mich.

[21] Appl. No.: 96,064

[22] Filed: Nov. 20, 1979

[51] Int. Cl.³ ............................................ A61H 23/00
[52] U.S. Cl. ........................................................ 128/54
[58] Field of Search ................ 128/53, 207.14, 207.15, 128/204.18, 204.24, 204.26, 204.28

[56] References Cited

U.S. PATENT DOCUMENTS

| | | | |
|---|---|---|---|
| 2,615,463 | 10/1952 | Burns | 128/53 |
| 2,774,346 | 12/1956 | Halliburton | 128/204.26 |
| 3,351,052 | 11/1967 | Hewson | 128/53 |
| 4,090,518 | 5/1978 | Elam | 128/207.15 |
| 4,150,676 | 4/1979 | Jackson | 128/207.15 |

*Primary Examiner*—William E. Kamm
*Attorney, Agent, or Firm*—Price, Heneveld, Huizenga & Cooper

[57] ABSTRACT

An improved cardiopulmonary resuscitator and method of cardiopulmonary resuscitation is disclosed which involves cyclically compressing a patient's chest and simultaneously ventilating the patient's lungs to a safe limiting pressure over a period of time encompassing at least one complete compression cycle. Retrograde and exhale flow from the patient's lungs is prevented during the systolic portion of the compression cycle providing for a pressure increase in the patient's thorax due to compression of the patient's chest. Simultaneous application of ventilation pressure to the patient's lungs and compression of the patient's chest creates a pressure increase in the patient's thorax during systole which enhances perfusion. Continuous application of ventilation pressure during the diastolic portion of the compression cycle insures good tidal volume and enhanced blood gas exchange. Since the high intrapulmonary pressures created by the technique are substantially equaled by intrathoracic pressures and there is no substantial difference of pressure across the alveoli, trauma that would normally occur due to generation of differential pressures of the magnitude created by this technique in the lungs is avoided. After the patient's lungs are ventilated to the predetermined limiting pressure over a period of time encompassing a predetermined number of compression cycles, the patient's lungs are vented to the atmosphere.

25 Claims, 6 Drawing Figures

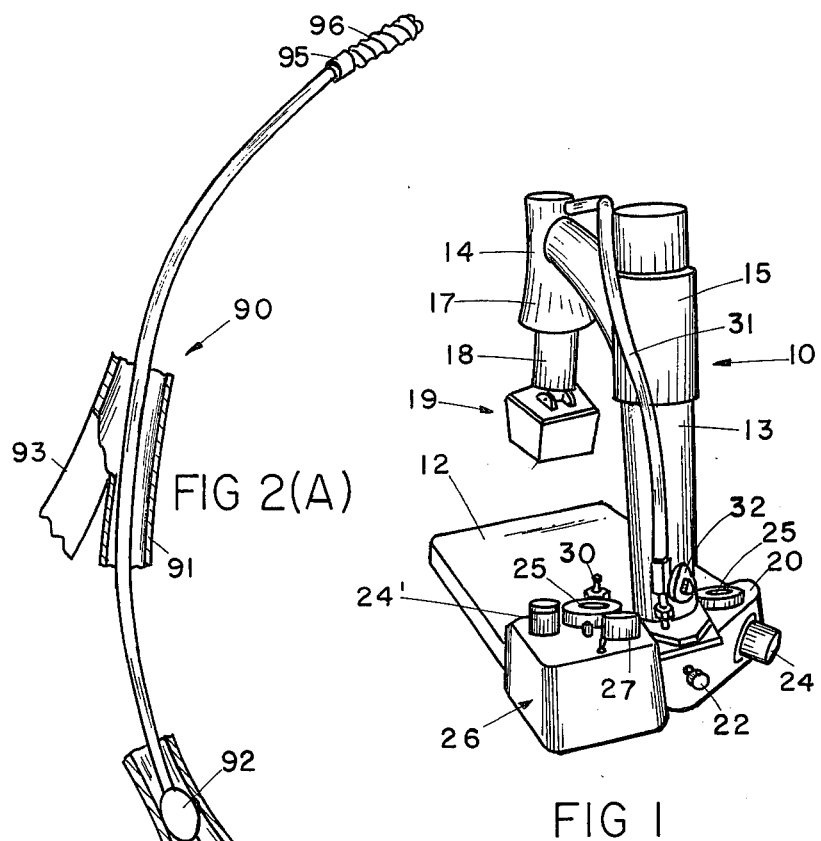
FIG 2(A)
FIG 1
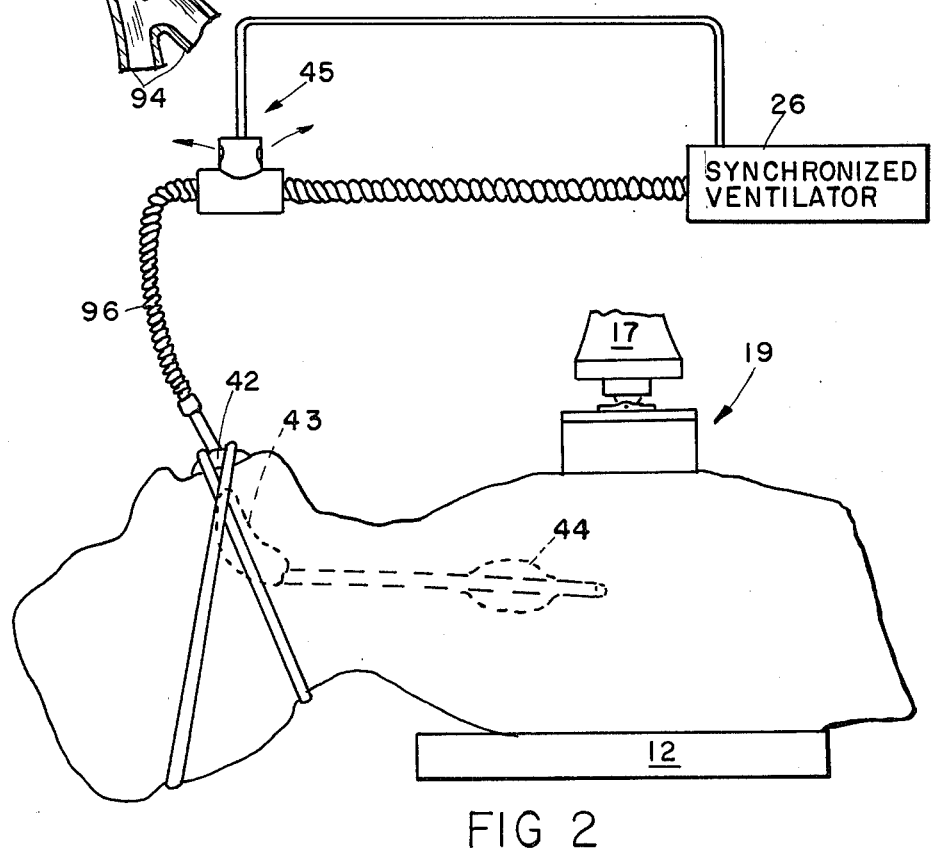
FIG 2

CPR PROTOCOL AND CARDIOPULMONARY RESUSCITATOR FOR EFFECTING THE SAME

BACKGROUND OF THE INVENTION

The invention relates generally to cardiopulmonary resuscitators and, more particularly, to an improved CPR protocol and cardiopulmonary resuscitator for affecting the same.

External cardiac compression can effectively be employed for obtaining perfusion by causing forced pumping of blood from a temporarily stopped heart. This is normally achieved by constant cyclic external compression of the heart (systole) for a short time period followed by pressure release to allow heart expansion (diastole) for a short time period. To achieve proper heart compression by external force, the breast bone is forced toward the backbone of the patient while the patient's back is rigidly supported.

Although forced pumping of blood is essential for a patient whose heart has stopped, this is only part of the continuous treatment necessary, since when the heart stops, breathing stops also. Hence, when external mechanical or manual cardiac compression is presently employed, simultaneous sustained cyclic mechanical or mouth to mouth ventilation is also important to cyclically inflate the lungs for oxygenization of the blood. According to accepted medical practice, the lungs are ventilated or inflated during the diastole period of the compression cycle. Whether carried out mechanically or manually, these techniques comprise what is commonly referred to as cardiopulmonary resuscitation or CPR.

The operating theory behind current CPR protocol is that cardiac compression produced by physical compression of the heart between the sternum and the spine of the patient, pressurizes the chambers in the heart driving blood through the one-way valves of the heart and through the vascular beds in the normal direction. During this process, the left side of the heart supplies oxygenated blood to the patient's body through the arterial system and the right side of the heart perfuses blood by directing blood through the pulmonary bed and back to the left heart. More recent findings however indicate that this is only an infrequent mechanism for perfusion and that the anatomy of an individual is important as to whether this mechanism works. Only patients with fairly large hearts and fairly small chest dimensions actually receive perfusion by this mechanism and data would indicate that this occurs in only twenty to thirty percent of patients. An alternate theory has developed to the effect that generally high intrathoracic pressures during external cardiac compression may be the primary mechanism for driving blood through the heart. Since intrathoracic pressure, or the pressure within the chest cavity defined by the rib cage, is also influenced by pressure within the patient's lungs, the mechanics of ventilation have become very important in producing perfusion. In particular, it has been found that by inflating the lungs during chest compression to fairly high pressures, that cardiac output is greatly enhanced.

This theory would explain recent developments such as "cough" CPR. During a typical cough, very high intrathoracic pressures are produced, and it has been found that blood is perfused by these high intrathoracic pressures created only by high pressures developed in the lungs and thorax by the muscle and valving action of the body during the act of coughing. And indeed, it has been demonstrated that cyclic coughing is a suitable technique for keeping a patient viable who has gone into ventricular fibrillation. As long as the patient can cough regularly, he can maintain himself in a viable state and conscious until help arrives. Of course, cough CPR is merely supportive therapy and definitive therapy such as defibrillation has to be applied quickly to save the patient. Cough CPR is only a very temporary procedure.

Others have found that ventilating intubated patients during every systolic period of CPR with relatively high pressures on the order of 100 to 150 centimeters of water greatly enhances cardiac output and yields adequate blood gases. Normally, these are considered dangerously high pressures that alone would cause trauma to the lungs. However, it has been found that when these ventilating pressures are precisely synchronized with the systolic portion of the chest compression cycle, the generally high intrapulmonary pressures are equalled by the intrathoracic pressures and there is no substantial difference of pressure across the alveoli. Thus, these relatively high ventilator pressures are regarded as safe if applied simultaneously with cardiac compression. In connection with this technique, observations have been made that the heart valves are frequently incompetent and therefore some other valving mechanism has to be found to account for the forward perfusion of blood. This is especially true for cerebral perfusion since all of the pressures acting on the vessels within the thoracic cage are basically identical. That is, central venous pressure is equal to aortic pressure which is equal to intrathoracic pressure. In connection with this, it has been observed that the veins leaving the thorax apparent collapse under these conditions and this creates a valving action, preventing retrograde venus flow through the upper main veins such as jugular vein, whereas the arterial lines stay open so that some blood is pushed into the arterial bed without an equivalent retrograde venous flow. Thus, it is apparently possible to create forward perfusion without the working of the cardiac valves. Problems with this CPR protocol involve the use of very high ventilation pressures which are not easily obtained with conventional resuscitators. Also, since the pressure used for ventilation is dangerously high, as a differential alveolar pressure, the application of these ventilation pressures must be precisely synchronized with elevated thoracic pressure during systole. For example, should the force on the chest be inadvertently reduced or should external cardiac massage be momentarily interrupted during ventilation, an extremely dangerous pulmonary differential pressure would be reached which might well be traumatic to the lungs. Furthermore, despite the use of high ventilation pressures with this technique, there is no certainty of the adequacy of established pulmonary differential pressures which are a measure of tidal volume needed to establish adequate gaseous exchange and to reduce atelectasis. That is to say, while this CPR technique would appear to improve the pumping of blood through the heart it has not always adequately oxygenated the patient's blood.

Another proposed technique for employing ventilation to enhance perfusion has involved using relatively benign ventilator pressures such as 20 to 30 centimeters of water. According to this technique, once external cardiac massage is established, this relatively benign ventilator pressure is applied to the lungs for three complete compression cycles and then the patient's lungs are vented to the atmosphere for two complete compression cycles in a continuous fashion. Although this technique has been found to enhance cardiac output and yield good blood gases, problems encountered with this CPR protocol include the fact that intrathoracic pressures are limited by forward ventilation pressure since retrograde or exhale flow is possible out ventilator control valves during chest compression. This severely limits pressure buildup in the lungs during the application of external cardiac massage and creates a limitation on cardiac output. Also, with this technique there of course would be no enhancement of intrathoracic pressure during the exhale period of the ventilatory cycle.

SUMMARY OF THE INVENTION

According to the present invention, an improved CPR protocol is presented which solves many of the problems encountered in prior art CPR protocols employing ventilation pressure to enhance cardiac output. More specifically, according to the method of the present invention, while the patient's chest is cyclically compressed, the patient's lungs are ventilated with a relatively benign limiting pressure over a period of time that encompasses at least one, and preferably several complete compression cycles. Retrograde flow to the ventilator and exhale flow from the patient's lungs is prevented during the systolic portion of the compression cycle thus providing for a substantial pressure increase or pressure spike in the patient's lungs due to external compression of the patient's chest. Furthermore, during the diastolic portion of the compression cycle the ventilator continues to add tidal volume to the lungs, creating good blood gas exchange. Thereafter and cyclically the patient's lungs are periodically vented to the atmosphere. This alternative CPR protocol eliminates the use of high ventilation pressures which can not be readily obtained with conventional resuscitators and eliminates the necessity of precisely synchronizing elevated ventilation pressures with elevated thoracic pressures during systole. Furthermore, adequate pulmonary differential pressures are assured for ventilation purposes and high intrathoracic pressures needed to enhance perfusion are no longer limited by the forward ventilation pressure, since retrograde and exhale flow is no longer possible during the systolic portion of the compression cycle. Although this technique still does not provide a method of enhancing intrathoracic pressure during the exhale period of the ventilatory cycle, it is presented as a compromise protocol which would have many advantages without the hazards encountered in prior art CPR protocols employing relatively high ventilatory pressures for enhancing cardiac output.

Apparatus for conducting the CPR protocol of the present invention comprises a reciprocal cardiac compressor means for cyclically compressing a patient's chest and a ventilating means for inflating the patient's lungs to a relatively benign limiting pressure over a period of time encompassing at least one cycle of the compressor means. Ventilator output control means is also provided which both prevents retrograde and exhale flow during the systolic portion of the cycle of the compression means, thus providing for a pressure increase in the patient's lungs due to external cardiac massage, and periodically vents the patient's lungs to the atmosphere.

BRIEF DESCRIPTION OF THE DRAWINGS

FIG. 1 is a perspective view of a cardiopulmonary resuscitator of the type employed in the present invention.

FIG. 2 is a schematic representation of the cardiopulmonary resuscitator of the present invention and a fragmentary elevational view illustrating the application of the present invention to the human body.

FIG. 2(a) is a partial sectional view of a patient's esophagus, trachea and bronchial tubes with an endotracheal tube installed in the patient's trachea.

DESCRIPTION OF THE PREFERRED EMBODIMENTS

Figure 3:
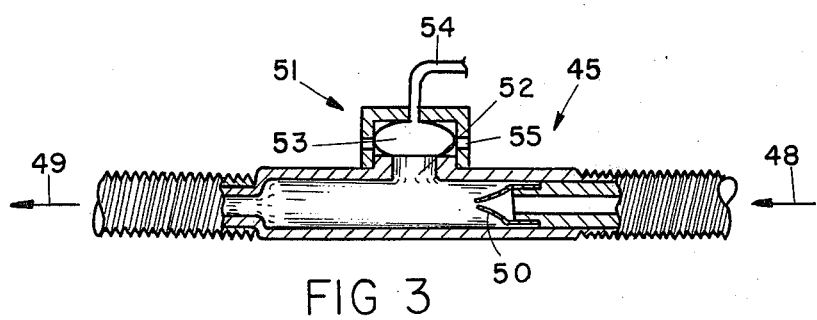
FIG. 3 is an elevational view of an active non-rebreathing ventilator control valve constructed according to the present invention.

Referring to FIG. 1, a combination cardiac compressor and ventilator or cardiopulmonary resuscitator unit is illustrated at 10. The CPR unit includes a platform 12 for supporting the back of the patient, a removable upstanding column or support 13 and an overhanging beam or arm 14 mounted to column 13 with a releasable collar 15. The outer end of arm 14 includes a pneumatic power cylinder 17 and an extendable plunger piston 18 and a compressor pad 19 for contacting and compressing a patient's sternum. The piston plunger 18 and compressor pad 19 are pneumatically operable to shift towards the platform 12 to compress the sternum and thus the heart of the patient resting in the supine position on the platform 12, as illustrated in FIG. 2. The piston and pad return with the normal expansion of the patient's chest. The platform 12 includes a thick hollow end 20 in which the support 13 is removably mounted and which includes an internal chamber that encloses a control valve assembly at 22. The control valve assembly repetitively applies pressure to the power cylinder to create a cyclical compression cycle. Protruding from the platform 20 is a pressure regulator knob 24 for controlling the pressure of the output of control valve assembly 22. A pressure indicating gauge is disposed at 25. A ventilator subassembly is disposed at 26 and is integrally mounted with the compressor with the exception of a breathing hose normally connected to air outlet 27 and a mask or tube for directing oxygen enriched air into the patient's lungs. A pressure regulator knob 24' and a gauge 25' are used to control the air pressure applied to the patient's lungs during ventilation. A CPR unit suitable for use with the present invention is essentially like that shown in U.S. Pat. No. 3,461,860 to Clare E. Barkalow and the disclosure of this patent is incorporated herein by reference.

Compressor cycles are controlled by the valve 22. Periodic output pulses of oxygen from the control valve 22 are allowed to pass to the ventilator 26. These pulses activate a programmer valve within the ventilator to turn it on periodically and the duration of the "on" cycle is regulated by a timer control. One of the advantages of this type of apparatus is that both the cardiac compressor and the ventilator of the CPR unit are pneumatically operated and pneumatically controlled. Thus, to set the device up, the only power source required is an external source of compressed gas, normally oxygen, which is connected to the unit by a gas hose attached to fixed connector 30. This supply of pressurized oxygen operates the entire CPR unit. Pressurized oxygen passes through the compressor control valve assembly 22 inside the cardiac compressor platform and then through hose 31 that extends to the upper end of cyclinder 17. A manual shutoff valve 32 may be provided to turn off the cardiac compressor manually while allowing the ventilator unit 26 to still operate on a cyclical basis. Oxygen also passes to a programmer, not illustrated, that is a pneumomechanical device serving to periodically open a passageway for a flow of oxygen to the ventilator at regular intervals. This programmer can be preset to provide flow of oxygen to the ventilator at regular multiples of compressor cycles (as done in most prior art CPR techniques), or may be preset to provide a pulse of oxygen at a preset limiting pressure that extends over a plurality of compressor cycles. Further details of the structure and operation of a CPR unit suitable for use with the present invention may be obtained from the aforementioned Barkalow patent.

Referring now to FIG. 2, it is illustrated that the ventilator schematically illustrated at 26 is connected to an oral and nasal seal 42 which is herein illustrated as an esophago-pharyngeal airway including a first bulbous inflatable cuff 43 for sealing the patient's oral and nasal cavities and a second bulbous inflatable cuff 44 for sealing the patient's esophagus. Such a sealing means has been disclosed and claimed previously in U.S. Pat. No. 4,090,518 entitled ESOPHAGO-PHARYNGEAL AIRWAY to James O. Elam. The esophago-pharyngeal airway disclosed by Elam has been found suitable with the present invention since it creates a good seal for preventing the escape of relatively high ventilatory pressures. The disclosure of the aforementioned Elam patent is hereby incorporated by reference. Referring now also to FIG. 2(a), another device suitable for use with the present invention, and well known to those skilled in the art, is an endotracheal tube 90. The endotracheal tube 90 is inserted in the patient's trachea 91 and includes an inflatable cuff 92 for creating a positive seal between the ventilator and the patient's lungs. The patient's bronchial tubes and esophagus are partially illustrated at 93 and 94, respectively. The endotrachel tube 90 normally extends outside of the patient's oral cavity (not illustrated in FIG. 2a) and includes a pressure fitting 95 for connecting the ventilator output tube 96 thereto. Ordinary ventilator masks designed for use with benign ventilatory pressures on the order of 20 to 30 centimeters of water are not thought to be suitable for use with the present invention since these masks can leak and prevent the buildup of high ventilatory pressures during external cardiac massage. Furthermore, these masks do not provide a positive seal preventing air flow into the patient's esophagus which is desirable to prevent regurgitation of digestive fluids during CPR. Thus, an airway such as the Elam device, an endotracheal tube, or the like is desirable to create a positive seal connecting the ventilator to the patient's lungs.

The output of the ventilator 26 is controlled by a ventilator output control means 45 which prevents retrograde flow back to the ventilator 26 and exhale flow from the patient's lungs during systolic portions of the compressor cycle. Blocking retrograde and exhale flow during systole provides a pressure increase in the patient's lungs due to compression of the patient's chest. The ventilator output control means 45 further serves to periodically vent the patient's lungs to the atmosphere. Referring now also to FIG. 3, it is illustrated that the ventilator output control means 45 preferably comprises an active non-rebreathing control valve. The control valve 45 is generally T-shaped in cross section receiving the output of the ventilator at 48 and delivering the ventilator output at 49 during the portion of the ventilatory cycle when pressure is being applied to the patient's lungs. The body of the control valve 45 includes a check valve 50 through which the output of the ventilator passes. The check valve 50 prevents retrograde flow from the patient's lungs back into the ventilator during chest compression. The valve 45 further includes a vent 51 for periodically venting the patient's lungs to the atmosphere. The vent 51 includes a vent port 52 and an inflatable bladder 53 normally covering and sealing the vent port 52. The inflatable bladder 53 is inflated by a tube 54 which delivers a control pressure from the ventilator. During portions of the ventilatory cycle when pressure is applied to the patient's lungs, a control pressure from the ventilator is directed to inflatable bladder 53 through tube 54 to pressurize the bladder 53 and effectively seal the vent port 52 preventing exhale flow from the patient's lungs. This insures the buildup of relatively high ventilatory pressures in the patient's chest during the systole portion of the compression cycle. At the end of the ventilatory cycle the control pressure applied by the tube 54 is removed and the bladder 53 deflates to provide for exhale or venting of the patient's lungs through port 52 and apertures 55 in the body of the valve 45.

Figure 4:
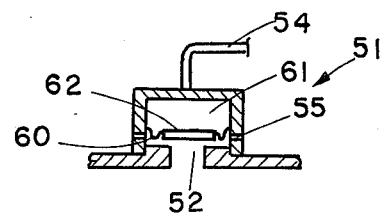
FIG. 4 is a partial elevational view of another active non-rebreathing ventilator control valve constructed according to the present invention.

Referring now to FIG. 4 an alternate embodiment of the vent 51 of control valve 45 is illustrated. In the case the vent 51 comprises a vent port 52 and a rolling diaphragm seal 60 which covers and seals the vent port 52 when pressure is applied to the chamber 61 above diaphragm 60 through tube 54. Rolling diaphragms are familiar to those skilled in the art and the diaphragm 60 illustrated herein includes a piston 62 for covering and sealing vent port 52.

The control pressure required for actuating the vent 51 of control valve 45 is obtained by tapping a flow of high pressure oxygen present in the pneumatic control circuit of the ventilator 26. More specifically, referring to the afornementioned Barkalow patent, the high pressure oxygen line 123 extending between the spool valve 115 and the venturi pump 56 may be tapped to provide a suitable control pressure for the control valve 45. Advantageously, high pressure oxygen is present in this line only when the ventilator is "on", or the ventilator is applying pressure to the patient's lungs.

Figure 5:
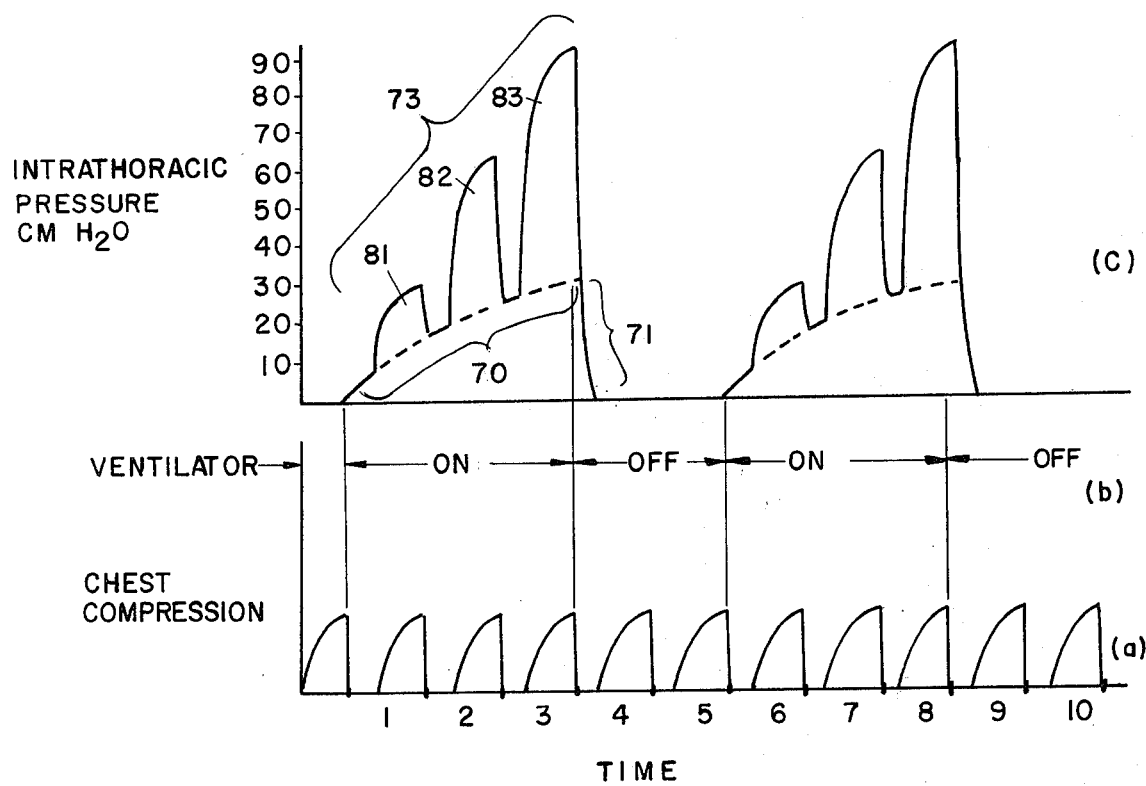
FIG. 5 is a plot of intrathoracic pressure ventilator function and chest compression versus time for the cardiopulmonary resuscitator of the present invention.

Referring now to FIG. 5, the CPR protocol of the present invention and the operation of the cardiopulmonary resuscitator of the present invention is explained in further detail. Plot (a) in FIG. 5 is a plot of chest deflection due to compression versus time. Plot (b) indicates the period of the ventilatory cycle when the limiting pressure of the ventilator is applied to the patient's lungs. Plot (c) is a typical representation of intrathoracic pressure in centimeters of water due to the simultaneous application of the limiting pressure of the ventilator and external chest compression. According to the present embodiment the ventilator is on for a period extending through three complete compressor cycles starting at the release of chest compression, or at the end of systole, in a previous compression cycle. Thereafter the ventilator pressure is removed from the patient's lungs and the patient's lungs are vented to atmosphere for a period of two complete systoles. At the end of the fifth complete systole counted from the initiation of the first ventilatory cycle, the ventilatory cycle is again repeated. In the present case, a relatively benign ventilator pressure of 30 centimeters of water is applied by the ventilator. If this ventilator pressure were applied to the patient's lungs alone without the simultaneous application of chest compression, pressure within the patient's lungs and thorax would build to a peak of thirty centimeters of water along a curve generally indicated by the broken curve 70 of plot (c). At the beginning of the exhale portion of the ventilatory cycle, the pressure in the patient's lungs and thorax would decrease quite rapidly as indicated by the solid line 71. However, simultaneous application of chest compression while preventing retrograde and exhale flow from the patient's lungs creates a series of pressure increases or spikes in the patient's lungs and thorax generally indicated by the curves 73. Reviewing the plot of intrathoracic pressure versus time, the solid curves represent the actual pressure in the patient's thorax due to the simultaneous application of the relatively benign ventilatory pressure of 30 centimeters of water and external chest compression, while the dotted or broken lines represent pressure that would normally exist in the patient's lungs and thorax due to ventilation alone. The two curves generally overlap except during the systole or compression portions of the compression cycle. The conventional compressor cycle which compresses the chest an amount approximately equal to 20 percent of the normal anterior to posterior thickness of the patient's chest is sufficient to generate the high intrathoracic pressures found desirable in the CPR protocol of the present invention. At the end of the third systole of the compression cycle, the patient's lungs are vented to the atmosphere by releasing pressure from inflatable bladder 53 in control valve 45 and the patient's lungs remain so vented to the atmosphere until the end of compression cycle number 5. Thereafter the ventilatory cycle is repeated.

More specifically, actual intrathoracic pressure may be related to the operation of the control valve 45 in the following manner. During the first ventilatory cycle and the first complete compression cycle, air entering into the patient's lungs during the first diastole is compressed during the following, or first systole, and there is a rapid buildup of intrathoracic pressure represented by the first spike of intrathoracic pressure 81 illustrated in plot (c). During the second diastole period the patient's chest relaxes and intrathoracic pressure is reduced to a level corresponding to the inflation pressure being presented by the ventilator. The spike 81 during the first systole is created because the check valve 50 of control valve 45 prevents retrograde flow from the patient's lungs back to the ventilator and the inflatable bladder 53 firmly seals vent port 52 preventing exhale from the patient's lungs to the atmosphere. Thereafter, subsequent pressure spikes 82 and 83 are created during the second and third systoles. At the end of the third systole the control pressure applied to the inflatable bladder of 53 through tube 54 is removed and the patient's lungs are allowed to vent to the atmosphere through vent port 52 and apertures 55 in the body of valve 45.

This method may be used to generate relatively high intrathoracic pressures in the range of 75 to 200 centimeters of water with the application of a limiting ventilation pressure of 10 to 60 centimeters of water. The method provides a CPR technique or protocol employing high intrathoracic pressures to enhance perfusion without many of the disadvantages attendant to prior art CPR protocols employing high ventilator pressures.

The above description should be considered as exemplary and that of the preferred embodiment only. For example, it is clear that the control valve 45 may be provided with a solenoid operated vent or the like for periodically venting the patient's lungs to the atmosphere in accordance with an electrical signal generated by the ventilator. It is also clear that the ratio of ventilatory cycles to compression cycles, the limiting pressure applied by the ventilator, the rate of incease of the limiting pressure applied by the ventilator and the degree of external chest compression applied may vary. Also, since the mechanical hyperventilation provided may, when the device is powered by 100% oxygen, produce blood chemistry abnormalities when used for a long period of time (excessive $CO_2$ "blow-off", respiratory alkalosis, hyperoxemia), under such circumstances, it may be desirable to switch the input to an appropriate oxygen/carbondioxide mixture. The true spirit and scope of the present invention should be determined by reference to the appended claims. It is desired to include within the appended claims all modifications of the invention that come within the proper scope of the invention.

The embodiments of the invention in which an exclusive property or privilege is claimed are defined as follows:

1. A cardiopulmonary resuscitator comprising in combination:
   a reciprocatable cardiac compressor means for cyclically compressing a patient's chest;
   a ventilating means for simultaneously inflating the patient's lungs to a benign limiting pressure over a period encompassing at least one cycle of said compressor means; and
   a ventilator output control means for:
   (i) preventing retrograde and exhale flow from the patient's lungs during the systolic portion of the cycle of said compressor means thus providing for a pressure increase in the patient's lungs due to compression of the patient's chest, and
   (ii) periodically venting the patient's lungs.

2. The cardiopulmonary resuscitator of claim 1 wherein said ventilator output control means comprises an active non-rebreathing control valve comprising:
   a check valve through which the output of said ventilating means passes; and
   a vent for periodically venting the patient's lungs to the atmosphere.

3. A cardiopulmonary resuscitator of claim 2 wherein said vent further includes means for pneumatically actuating said vent.

4. The cardiopulmonary resuscitator of claim 3 wherein said vent comprises:
   a vent port;
   an inflatable bladder; and
   means for applying pressure to said bladder to expand the same to cover and seal said vent port.

5. The cardiopulmonary resuscitator of claim 3 wherein said vent comprises:
   a vent port;
   a pressurizable chamber disposed adjacent said vent port;
   a rolling diaphragm disposed in said chamber; and means for applying pressure to said pressurizable chamber and urging said rolling diaphragm into a sealing relationship with said vent port.

6. The cardiopulmonary resuscitator of claim 1 wherein said compressor means and said ventilating means further include means for pneumatically driving and controlling said compressor means and said ventilating means.

7. The cardiopulmonary resuscitator of claim 1 wherein said ventilating means includes sealing means comprising an oral cuff adapted for disposition at the rear of the patient's oral cavity for sealing the patient's nasal passages at the soft palate.

8. The cardiopulmonary resuscitator of claim 7 wherein said sealing means comprises an esophago-pharyngeal airway.

9. The cardiopulmonary resuscitator of claim 1 wherein said ventilating means includes sealing means comprising an endotracheal tube.

10. The cardiopulmonary resuscitator of claim 1 wherein said limiting pressure is in a range of 10 to 60 cm of water.

11. The cardiopulmonary resuscitator of claim 1 wherein said compressor means comprises means for compressing the patient's chest to a peak intrathoracic pressure in a range of 75 to 200 cm of water.

12. The cardiopulmonary resuscitator of claim 1 wherein said ventilating means comprises means for supplying said limiting pressure over a period of time encompassing a plurality of compression cycles or fractions thereof.

13. The cardiopulmonary resuscitator of claim 12 wherein said ventilating means comprises means for supplying said limiting pressure over a period of time encompassing three complete compression cycles.

14. A cardiopulmonary resuscitator of claim 12 wherein said control means comprises means for periodically venting the patient's lungs over a period of time encompassing a plurality of compression cycles, or fractions thereof.

15. The cardiopulmonary resuscitator of claim 14 wherein said control means comprises means for periodically venting the patient's lungs over a period of time encompassing two complete compression cycles.

16. A method for conducting cardiopulmonary resuscitation comprising the steps of:
cyclically compressing a patient's chest;
simultaneously ventilating the patient's lungs to a benign limiting pressure over a period of time encompassing at least one compression cycle;
preventing retrograde and exhale flow during the systolic portion of the compression cycle thus providing for a pressure increase in the patient's lungs due to compression of the patient's chest; and
periodically venting the patient's lungs.

17. The method of claim 16 wherein said limiting pressure is in a range of 10 to 60 cm of water.

18. The method of claim 16 wherein, during said compressing and said ventilating steps, the patient's chest is compressed to a peak intrathoracic pressure in a range of 75 to 200 cm of water.

19. The method of claim 18 wherein, during said compressing and said ventilating steps, said limiting pressure is applied over a period of time encompassing a plurality of compression cycles or fractions thereof.

20. The method of claim 19 wherein, during said compressing and said ventilating steps, said limiting pressure is applied over a period of time encompassing three complete compression cycles.

21. The method of claim 19 wherein the patient's lungs are periodically vented over a period of time encompassing a plurality of compression cycles or fractions thereof.

22. The method of claim 21 wherein the patient's lungs are periodically vented over a period of time encompassing two complete compression cycles.

23. The method of claim 16 further including the step of intubating the patient before ventilating the patient's lungs.

24. The method of claim 16 further including the step of forming a positive seal between the patient's lungs and a ventilator with an esophago-pharyngeal airway before ventilating the patient's lungs.

25. The method of claim 16 further including the step of forming a positive seal between the patient's lungs and a ventilator with an endotrachael tube before ventilating the patient's lungs.

* * * * *